United States Patent [19]

Perler

[11] Patent Number: 5,062,833
[45] Date of Patent: Nov. 5, 1991

[54] NON-REUSABLE DISPOSABLE SYRINGE AND LOCKING DEVICE

[76] Inventor: Robert F. Perler, 175 Memorial Hwy., Ste 1-6, New Rochelle, N.Y. 10801

[21] Appl. No.: 603,135

[22] Filed: Oct. 25, 1990

Related U.S. Application Data

[63] Continuation-in-part of Ser. No. 334,710, Apr. 6, 1989, Pat. No. 4,986,812.

[51] Int. Cl.⁵ .............................................. A61M 5/00
[52] U.S. Cl. ..................................... 604/110; 604/218
[58] Field of Search ................ 604/110, 187, 218, 220

[56] References Cited

U.S. PATENT DOCUMENTS

| | | | |
|---|---|---|---|
| 4,212,309 | 7/1980 | Moorehead | 604/220 X |
| 4,267,846 | 5/1981 | Kontos | 604/220 X |
| 4,731,068 | 3/1988 | Hesse | 604/218 X |
| 4,820,272 | 4/1989 | Palmer | 604/110 |

Primary Examiner—John D. Yasko
Attorney, Agent, or Firm—Handal & Morofsky

[57] ABSTRACT

A non-reusable disposable syringe utilizing a conventional syringe body, a locking device allowing one full retraction of the plunger and one full expulsion of the contents wherein the locking device cooperates with the plunger shaft in advancing the piston in the expulsion stroke.

19 Claims, 4 Drawing Sheets

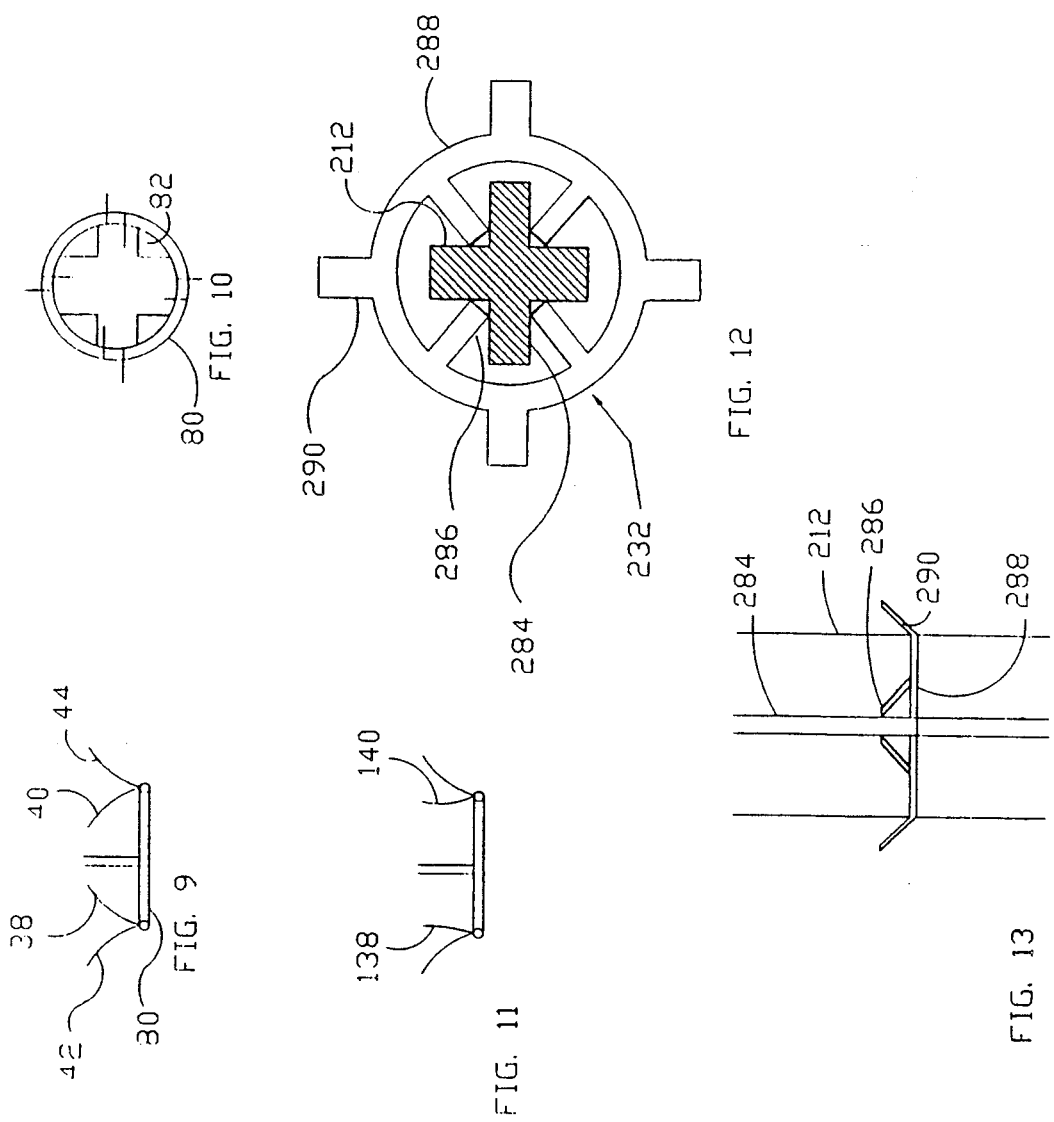

NON-REUSABLE DISPOSABLE SYRINGE AND LOCKING DEVICE

CROSS-REFERENCE TO RELATED APPLICATIONS

This application is a continuation-in-part of copending U.S. patent application Ser. No. 334,710 of Dr. Robert F. Perler, filed Apr. 6, 1989 and entitled LOCKING DEVICE PREVENTING REUSE OF A DISPOSABLE SYRINGE now U.S. Pat. No. 4,986,812.

BACKGROUND

The increasing awareness of the importance of sterility in hypodermic devices, coupled with the continually increasing number of hypodermic injections given, has led to the advent of disposable syringes. The initial sterility and low cost of disposable syringes has led to the widespread use of these syringes and the preference for disposable syringes over the older reusable glass syringes that require sterilization before each use.

The disposable syringe, by its very nature, has spawned problems. The disposable syringe is cheap and disposable and controls on the inventory of a cheap and plentiful item tend to loosen while controls on discarded items have generally been lax. It is not uncommon for syringes, along with the attached needles, to find their way into unauthorized hands. The syringes may be reused without sterilization and thereby contribute to a problem they originally were designed to prevent, i.e. the spread of disease due to contamination.

An unfortunately common unauthorized use of syringes is associated with the use of illegal drugs. The common practice of sharing the syringe among drug users dramatically increases the risk of exposure to, and spread of, disease.

Hepatitis has long been associated with illegal drug use as it is spread among users of injectable drugs via contaminated hypodermic devices. Today it is known that the Human Immune Virus associated with AIDS is spread similarly. Indeed, the highest rate of infection of AIDS is now found in intravenous drug users and the infection rate is increasing.

Non-reusable syringes will not stop drug use but can prevent sharing of contaminated needles and thus help fight the spread of diseases such as AIDS.

Non-reusable syringes have been designed in the past; however, there are numerous shortcomings in these earlier versions. Non-retractable drive shaft or piston arrangements such as found in Butterfield, U.S. Pat. No. 4,493,703, require pre-filled syringes as the syringe may not be filled by the user in the conventional manner. Lip-and-catch mechanisms of many sorts have been proposed, however until the lip-and-catch engages, the drive shaft and piston may retract and reuse is possible. Hesse, U.S. Pat. No. 4,731,068 requires a catch to be fixedly mounted and engage a slidable sheath thus requiring additional parts within the syringe, other embodiments require a plurality of cooperating parts that add to the complexity, assembly and cost of the syringe.

Owing to the problems or costs of the previous non-reusable syringes there has been no widespread acceptance and use of these devices in the medical community.

SUMMARY OF THE INVENTION

The invention is intended to provide a remedy, retaining the advantages of sterility and low cost of the disposable syringe and incorporating a locking device preventing reuse. The device cooperates with the plunger, the piston and the syringe allowing filling, discharging and aspiration while preventing reuse and some forms of partial use or misuse.

BRIEF DESCRIPTION OF THE DRAWINGS

One way of carrying out the invention is described in detail below with reference t drawings which illustrate only exemplary specific embodiments of the invention and in which:

FIG. 9 is a cross-section of a locking device compatible with the syringe of FIGS. 1 through 6;

FIG. 10 is a top view of a locking device;

FIG. 11 is a cross-section of a locking device compatible with the syringe of FIGS. 7 and 8;

FIG. 12 illustrates a locking device in plan;

FIG. 13 is a view along lines 13—13 of FIG. 12;

BEST MODE FOR CARRYING OUT THE INVENTION

Figure 1:
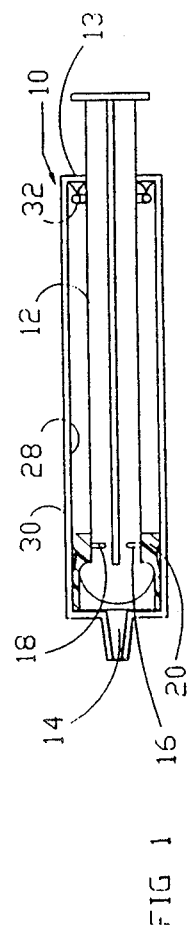
FIG. 1 is a view of the inventive syringe in the initial empty condition.

Referring to FIG. 1, the structure of the inventive syringe 10 is seen to comprise a plastic plunger shaft 12 integral with the plunger head 14, which is larger in diameter than the shaft, the shaft defining slots 16 and 18 to cause a weak area in the shaft forming a frangible portion. Shaft 12 is formed with a cross-section of a cross. A rubber piston 20 bears sealingly against the inner syringe wall 28 of a conventional syringe body 30. The plunger head fits within and sealingly conforms to a piston recess 22, best illustrated in FIGS. 2 and 3, the rear lip 24 of plunger head 14 bearing against the recess seat 26. A shaft stabilizer 13 is secured at the end of syringe body 30 to keep the shaft 12 from becoming decentered in body 30.

Figure 2:
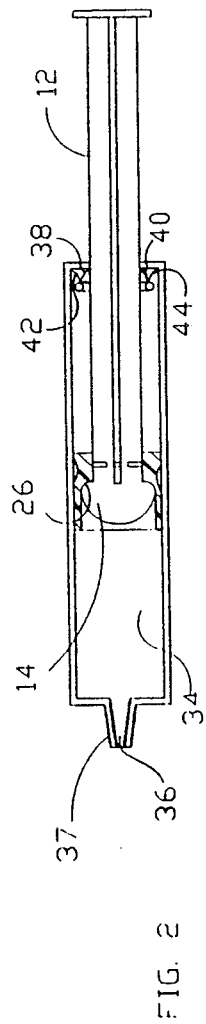
FIG. 2 is a cross-section of the syringe in FIG. 1 during the filling movement.

A spring locking device 32 is positioned at the rear of the syringe body in the initial, empty condition as illustrated in FIG. 1. In this position, the plunger head 14 is in the forward portion of the syringe body 30. When it is desired to use the inventive syringe, shaft 12 is pulled backwards, to draw the medicinal fluid into the syringe. FIG. 2 illustrates the plunger moving backwards. Plunger head 14 is pulled tight against recess seat 26 forming a seal and therefore reducing the pressure in the syringe interior 34 during backwards motion in the direction indicated by arrow 35, drawing a fluid into the syringe interior through a needle orifice 36 within a needle support 37. Plunger shaft 12 moves backwards easily over back-facing shaft prongs 38 and 40 of the locking device because they are oriented in the same direction as relative movement of shaft 12, while back-facing syringe prongs 42 and 44 prevent backward motion of the locking device 32 with respect to the syringe by digging into the inner syringe wall because they are pointed against the direction of relative movement of inner syringe wall 28. These prongs may terminate in a point to enhance their bite into the inner wall.

Figure 3:
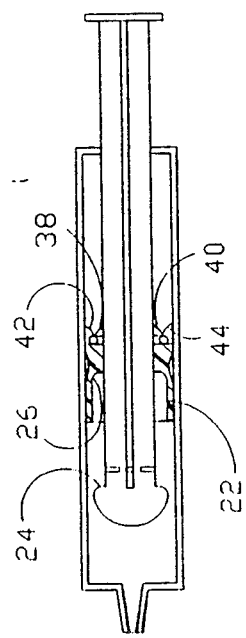
FIG. 3 is a cross-section of the syringe in FIG. 1 showing the result of an attempted premature discharge.

Forward motion of the plunger before complete retraction causes the plunger head to leave its position against recess seat 26 breaking the seal and leaving piston 20 in its position as illustrated in FIG. 3, causing leakage of the contents. FIG. 3 shows the positions of the locking device and the piston based upon forward motion of the shaft from the respective positions illustrated in FIG. 2.

Figure 4:
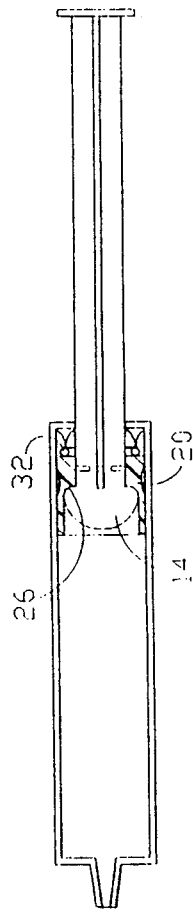
FIG. 4 is a cross-section of the syringe in FIG. 1 showing the plunger fully retracted.

After the completion of retraction, piston 20 is firmly secured between locking device 32 and plunger head 14. The forward motion of shaft 12 causes shaft 12 to engage shaft prongs 38 and 40. These prongs may also have pointed ends. FIG. 4 depicts the inventive syringe with shaft 12 fully retracted. Plunger head 14 is sealingly engaged against recess seat 26, and piston 20 is in forced contact with locking device 32. Engagement of prongs 38 and 40 during forward motion moves locking device 32 forward with the shaft as syringe prongs 42 and 44 allow forward motion of the locking device with respect to the syringe because they do not engage the wall 28 due to a reversal of the relative motion involved. Since the prior rearward motion of shaft 12 has brought the locking device into contact with the piston, as illustrated in FIG. 4, during forward motion the forward surface of the locking device move the piston forward with the shaft.

Figure 5:
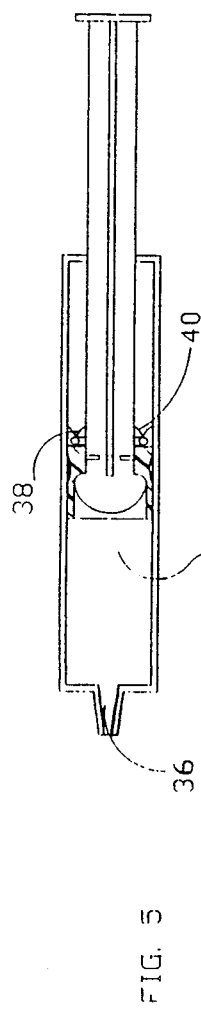
FIG. 5 is a cross-section of the syringe in FIG. 1 during the discharge motion.

As the plunger shaft is moved forward to discharge the medicine into the patient, prongs 38 and 40 hold the locking device in forced contact with piston 20 and plunger head 14 remains sealingly engaged against recess seat 26. The plunger shaft and head, the locking device and the piston move as a unit pressuring the contents of syringe interior 34 to move through needle orifice 36. As illustrated in FIG. 5, the locking device is moved forward by the shaft as shaft prongs 38 and 40 will not allow forward motion of the shaft with respect to the locking device. It is locking device 32 that drives piston 20 forward as the shaft is moved forward. Locking device 32 is, in turn, driven by shaft 12.

Figure 6:
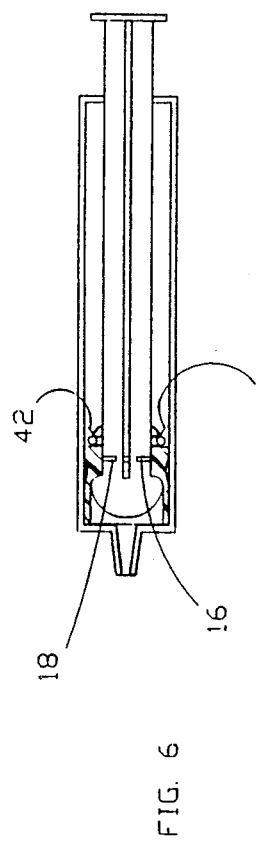
FIG. 6 is a cross-section of the syringe in FIG. 1 after complete discharge.

FIG. 6 shows the syringe completely discharged. Syringe prongs 42 and 44 prevent backward motion of the locking device and therefore also prevent the backward motion of the shaft and the piston. No further function is possible Slots 16 and 18, forming the break-away construction, permit the shaft to break before the locking device moves in the situation where excess force is used in an attempt to retract the piston a second time.

Figure 7:
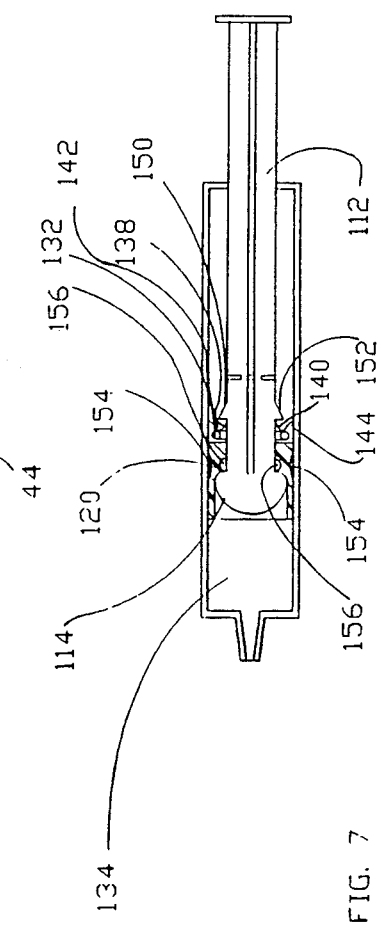
FIG. 7 is a cross-section of a second embodiment of the inventive syringe during the discharge motion.

An alternative embodiment incorporates a piston which allows aspiration. In this embodiment, as illustrated in FIG. 7, shaft prongs 138 and 140 are modified so that no biting or digging engagement may take place with respect to plunger shaft 112. Engagement of prongs 138 and 140 with plunger shaft 112 occurs by means of catches 150 and 152 positioned on shaft 112. When prongs 138 and 140 engage catches 150 and 152, respectively, the locking device 132 abuts piston 120 in the same manner as locking device 32 abuts piston 20 in FIGS. 4, 5 and 6, allowing the discharge of the fluid in the syringe interior 134. Generally, after filling, a small amount of medicine will be discharged together with any air bubbles to put the syringe in the position illustrated in FIG. 7.

Figure 8:
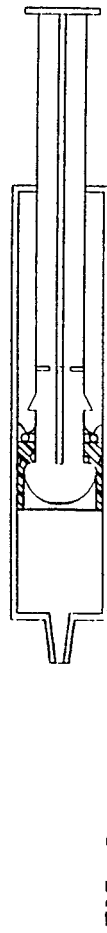
FIG. 8 is a cross-section of the syringe in FIG. 7 during aspiration.

In this embodiment, piston 120 is longer than the piston of the first embodiment and has an external annular indent 154 and an internal annular hollow 156. The piston material between annular indent 154 and annular hollow 156 is sufficiently solid to hold the plunger head sealingly engaged to the piston when the assembly is advancing, the piston being pushed along by the locking device engaged on catches 150 and 152. The annular indent and the annular hollow do, however, sufficiently increase the deformability of the piston at this point to allow a flexing if the plunger head provides a backward force on the piston, as illustrated in FIG. 8. During aspiration, a backward force is applied by retracting the plunger shaft. Aspiration is a means of determining whether or not the needle is in a blood vessel. Backward motion of the shaft, to the extent allowed by the piston flexing between indent 154 and hollow 156, is allowed by prongs 138 and 140 while prongs 142 and 144 hold the locking device stationary with respect to the syringe. Such backward motion will result in visibly drawing blood into the syringe if the needle is in a blood vessel.

Forward movement as a result of the release of the previously applied pressure on shaft 112 follows aspiration and allows the piston to return to the unflexed position as prongs 138 and 140 allow the shaft to move forward with respect to the locking device until catches 150 and 152 are reencountered In this manner, aspiration may be achieved without affecting the single-use quality of the syringe or the basic mechanism employed to achieve the single-use aspect of the inventive syringe.

The locking device may consist of a ring 80 or other shape allowing the plunger shaft to pass through its center with resilient wire prongs attached to the ring, as illustrated in FIGS. 9 and 10. Alignment members 82 may also be incorporated. flattened or planar members may be used instead of wire. The ring may be constructed of metal or plastic, the prongs are preferably formed from metal. The wire used may be spring steel and may be welded or soldered to a metal ring or may be stamped integrally therewith The prongs may be pointed to enhance their "biting" ability.

However, in the case of the embodiment shown in FIGS. 7 and 8, sharpening of the inner-directing, shaft prongs such as 138 and 140 is to be avoided (FIG. 11). Additionally, the prongs are to be shaped to avoid digging into the cylindrical shaft but capable of engaging the catches positioned on the shaft.

A self-aligning stamped star-washer type of locking member 232 is illustrated in FIG. 12. Here the shaft 212, shaped as a cross in cross-section has inner rounded surfaces 284 which engage inner gripping members 286 mounted on ring 288 which is integral with outer gripping member 290. As can be seen from FIG. 13, locking member 232 can be stamped from reliant sheet metal.

The slots forming the frangible portion of the shaft may be placed behind the point where the locking device prongs engage the shaft so that the break-away construction may serve to prevent forced twisting of the shaft to loosen the bite that the locking device may have on the cylinder or shaft, as illustrated in phantom lines in FIG. 7 and 8. In this manner, the shaft will separate into two parts before the twisting motion is significantly transferred to the locking device which may adversely affect the device's function.

The syringe and the plunger shaft are constructed of the normal materials associated with disposable syringes now in use, i.e. plastics or polymers and copolymers such as polyethylene, polypropylene, polystyrene, polybutylstyrene, etc.

Figure 14:
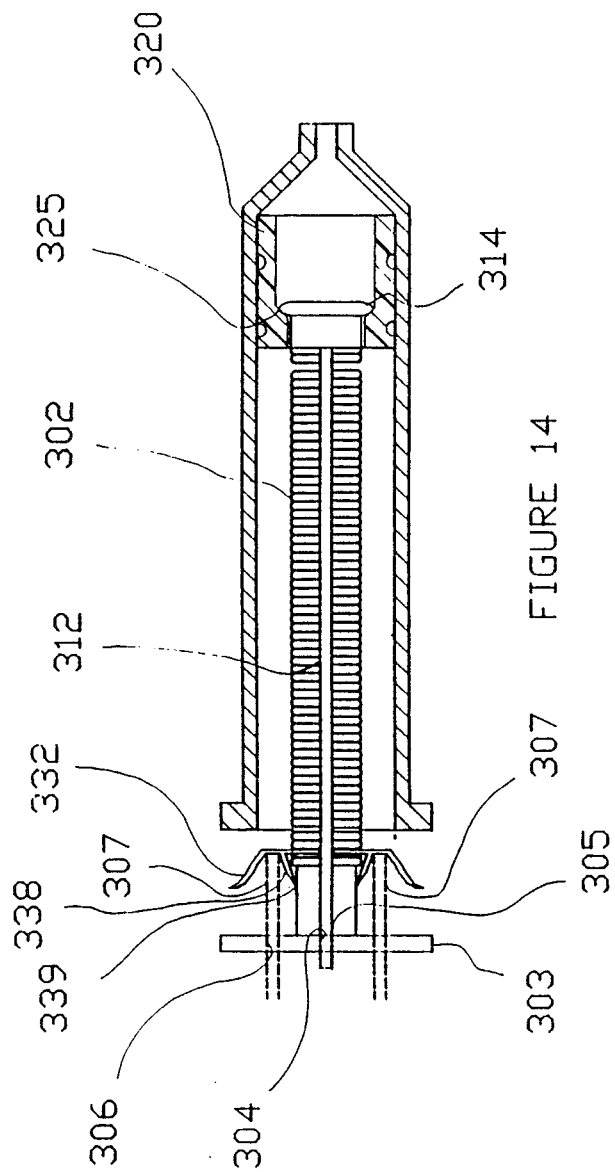
FIG. 14 is a view of an alternate embodiment plunger, piston and locking device group in a sectioned syringe body.

FIG. 14 shows a plunger shaft 312 that is longer than the syringe body, has texturing or ridging 302 along most of the shaft's length and a modified external shaft end 303.

Figure 15:
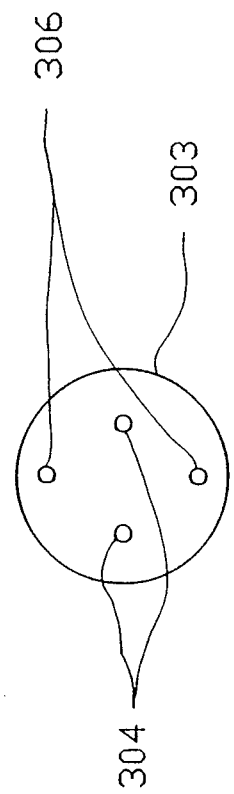
FIG. 15 is a plan view of the external shell end of the embodiment shown in FIG. 14.

Plunger shaft 312 is long enough to allow piston 320 to be fully inserted into the syringe while not causing locking device 332 to engage the syringe body. This allows for siliconization of the syringe body and seal by the moving of the plunger through the body a requisite number of times before use. Rods 305 are inserted in holes 304 to push piston 320 forward without the contact of locking device 332. The use of two rods 305 in holes 304 of FIG. 15 provide adequate and balanced pushing to advance piston 320.

In this embodiment, both shaft 312 and locking device 332 may be molded out of hard plastic and molded as a single unit. The locking device and shaft may be joined during molding at points 339 where shaft prongs 338 meet shaft 312. Inserting straight rods 307 (illustrated in phantom lines) through holes 306 to contact locking device 332 and then applying pressure will break the locking device 332 and shaft 312 apart at points 339. Ridging or texturing 302 will insure a locking relationship between locking device 332 and shaft 312 even if shaft prong 338 is not particularly sharp due to uneven breaking of the one piece molded subassembly.

After lubrication, holes 306 are used to advance the locking device into the syringe body to the position illustrated in FIG. 1. This approach can be used equally in the case of a one-piece plastic locking device-shaft unit or a separate plastic or metal locking device Rods 307 pass through holes 306 to engage the locking device and make the syringe non-reusable. Locking device 332 may be advanced to any desired position within the syringe to limit the syringe capacity to draw in fluid and therefore prevent waste.

Contact between plunger head 314 and piston 320 at surface 325 should be angled to generate perpendicular compression forces in order to comply with FDA pressure requirements.

Ridging 302 makes the shaft wider over the portion of the shaft that fits within the syringe body. The purpose of the ridging may be accomplished by merely making this section of the plunger shaft wider than the portion that does not enter into the syringe body. The extra width will cause more pressure between the shaft prongs and the shaft.

While an illustrative embodiment of the invention has been described above, it is, of course, understood that various modifications will be apparent to those of ordinary skill in the art. Such modifications are within the spirit and scope of the invention, which is limited and defined only by the appended claims.

I claim:

1. A non-reusable disposable syringe comprising:
   (a) a syringe body having an open end and defining an inside surface;
   (b) a plunger adapted to be positioned within said syringe body and to extend from said syringe body, said plunger comprising a plunger shaft and a plunger head at the end of said shaft adapted to be positioned in said syringe body, the shaft end on the other end of said shaft defining spaces for accepting a holding member to be positioned in said syringe body together with said plunger;
   (c) a cylindrical piston dimensioned and configured such that said piston bears sealingly against the inside, surface of said syringe body said piston being adapted to be positioned within said syringe body, said piston defining a central passage, a portion of said central passage being smaller than said plunger head, and said central passage being configured and dimensioned to sealingly engage and be closed by said plunger head, said piston being positioned within said syringe body with said plunger passing into said central passage, said piston being adapted to receive said holding member and be urged by said holding member against said plunger head; and
   (d) a locking device supported for slidable movement with respect to said plunger, said locking device being capable of movement with respect to said plunger in one direction only and capable of movement with respect to said syringe body in only one direction, said locking device being configured and dimensioned to advance said piston with said plunger after said piston is brought into contact with said locking device.

2. A syringe as in claim 1, wherein said spaces are holes defined in an end member disposed on the other end of said shaft.

3. A syringe as in claim 2, wherein said shaft has an irregular surface.

4. A syringe as in claim 1, wherein said shaft has an irregular surface.

5. A non-reusable disposable syringe comprising:
   (a) a syringe body having an open end and defining an inside surface;
   (b) a plunger comprising a ridged plunger shaft, said shaft being longer than said syringe body, a plunger head and a shaft end defining a plurality of holes;
   (c) a cylindrical piston dimensioned and configured such that said piston bears sealingly against the inside surface of said syringe body said piston being positioned within said syringe body, said piston defining a central passage, a portion of said central passage being smaller than said plunger head, and said central passage being configured and dimensioned to sealingly engage and be closed by said plunger head, said piston being positioned within said syringe body with said plunger passing into said central passage; and
   (d) a locking device supported for slidable movement with respect to said plunger, said locking device being capable of movement with respect to said plunger in one direction only and capable of movement with respect to said syringe body in only one direction, said locking device being configured and dimensioned to advance said piston with said plunger after said piston is brought into contact with said locking device.

6. A non-reusable disposable syringe as claimed in claim 5, wherein said locking device comprises
   (a) a base, proportioned to fit within said syringe body, said base defining a central opening sufficiently large such that said plunger shaft may pass through said opening;

(b) a plurality of syringe prongs integrally associated with said base, extending from said base in an axial direction and radially outwardly to an extent that at least one of said syringe prongs contact said syringe body when said locking device is positioned in said syringe body; and (c) a plurality of shaft prongs integrally associated with said annular base, extending from said base in the same axial direction as said syringe prongs and also extending radially inwardly to an extent that at least one of said shaft prongs will contact said plunger shaft when said plunger shaft is within said central opening.

7. A non-reusable disposable syringe as in claimed in claim 5, wherein said plunger shaft defines a break-away construction.

8. A non-reusable disposable syringe as in claimed in claim 6, wherein said axial direction extends toward the open end of said syringe body.

9. A non-reusable disposable syringe as claimed in claim 8, wherein said plunger head initially substantially abuts a closed end of said syringe body opposite said open end, and wherein said locking device is positioned adjacent and outside said open end.

10. A non-reusable disposable syringe as claimed in claim 7, wherein said break-away construction comprises slots cut into said plunger shaft.

11. A non-reusable disposable syringe as claimed in claim 5, wherein said locking device comprises four syringe prongs and four shaft prongs.

12. A non-reusable disposable syringe a claimed in claim 5, wherein said syringe prongs have sharp pointed tips.

13. A non-reusable disposable syringe as claimed in claim 5, wherein said plurality of holes are configured, dimensioned and positioned to permit rods to pass through said shaft end and contact said piston for the purpose of siliconization.

14. A non-reusable disposable syringe as claimed in claim 5, wherein said plunger and said locking device are formed of hard plastic as a single unit.

15. A non-reusable disposable syringe as claimed in claim 14, wherein said plurality of holes comprise at least two holes configured, dimensioned and positioned to permit rods to pass through said shaft end and contact said piston for the purpose of securing said piston for siliconization and at least one additional hole to allow insertion of a rod to apply pressure to said locking device and cause said plunger and said locking device to separate into two separate units.

16. A non-reusable disposable syringe as claimed in claim 5, wherein said ridged plunger shaft is ridged only over the portion of said shaft that enters said syringe body when said shaft is advanced into said syringe body.

17. A non-reusable disposable syringe as claimed in claim 16 wherein the ridged portion of said ridged plunger shaft is wider than the unridged portion.

18. A non-reusable disposable syringe as claimed in claim 3, wherein said irregular plunger shaft is ridged only over the portion of said shaft that enters said syringe body when said shaft is advanced into said syringe body.

19. A non-reusable disposable syringe as claimed in claim 3, wherein said irregular portion of said ridged plunger shaft is wider than the regular portion.

* * * * *